US008794241B2

(12) United States Patent
Dal Monte

(10) Patent No.: US 8,794,241 B2
(45) Date of Patent: Aug. 5, 2014

(54) RELAXANT DEVICE OF MUSCLE FASCICLES IN THE CERVICAL DISTRICT

(75) Inventor: Antonio Dal Monte, Rome (IT)

(73) Assignee: NBS Suisse Sagl, Lugano (CH)

( * ) Notice: Subject to any disclaimer, the term of this patent is extended or adjusted under 35 U.S.C. 154(b) by 463 days.

(21) Appl. No.: 12/444,492

(22) PCT Filed: Oct. 5, 2007

(86) PCT No.: PCT/IB2007/054061
§ 371 (c)(1), (2), (4) Date: Apr. 6, 2009

(87) PCT Pub. No.: WO2008/041205
PCT Pub. Date: Apr. 10, 2008

(65) Prior Publication Data

US 2010/0024829 A1 Feb. 4, 2010

(30) Foreign Application Priority Data

Oct. 6, 2006 (IT) .............................. MI2006A1923
May 14, 2007 (IT) ............................. MI20070180 U

(51) Int. Cl.
*A61G 15/00* (2006.01)
*A61F 7/00* (2006.01)
*A63B 21/065* (2006.01)

(52) U.S. Cl.
USPC ............................ 128/845; 607/109; 482/105

(58) Field of Classification Search
USPC ............... 198/DIG. 15; 2/170, 411, 413, 171; 482/92, 105, 10, 93, 11; 601/39, 79; 607/109, 110, 139
See application file for complete search history.

(56) References Cited

U.S. PATENT DOCUMENTS 4,632,389 A * 12/1986 Moss ............................ 482/105
6,110,080 A * 8/2000 Niv ............................... 482/105
7,708,673 B2 * 5/2010 Gibson-Horn ................ 482/105
2002/0169376 A1 * 11/2002 Pettibon ........................ 600/427
2003/0073549 A1 4/2003 Hatch
2004/0163162 A1 8/2004 Benziger

FOREIGN PATENT DOCUMENTS

DE 1 040 810 10/1958
DE 9409209 10/1995
JP 2003135499 A 5/2003

OTHER PUBLICATIONS

International Search Report dated Feb. 13, 2008, from corresponding PCT application.

* cited by examiner

*Primary Examiner* — Patricia Bianco
*Assistant Examiner* — Tarla Patel
(74) *Attorney, Agent, or Firm* — Young & Thompson

(57) ABSTRACT

The invention concerns a relaxant device of the cervical spine muscles of a human being, consisting of counterweight (c) and relative support (10, 11, 12) on a skull, suitable to arrange the counterweights in the rear part of the skull, the counterweights being such as to substantially balance the weight of the skull with respect to the rotation fulcrum thereof.

12 Claims, 2 Drawing Sheets

RELAXANT DEVICE OF MUSCLE FASCICLES IN THE CERVICAL DISTRICT

BACKGROUND OF THE INVENTION

1. Field of the Invention

The present invention concerns a relaxant device of the muscle fascicles suitable for preventing and reducing the symptoms due to inflammation of the cervical tract.

2. Description of the Related Art

As known, one of the parts of the human body which most frequently is a source of pain and functional inability, even regardless of traumatic events, is the cervical tract of the vertebral column.

The origin and development of these symptoms are most diverse, but they often occur in apparently healthy and non-traumatised individuals, hence in a large portion of the population.

As a matter of fact, the cervical column is an anatomically rather complex apparatus; it is restrained by a number of strong ligaments, which keep together the individual vertebral segments, and it is embedded in a muscular apparatus supporting and moving in coordination and harmoniously the entire spine and the head. The main muscles involved in this portion of spine are the trapezius muscles, which support the neck and the head, and the sternocleidomastoid, which control the rotation thereof. Next to these main muscles there exists a number of other small muscle fascicles, such as the four pairs of muscles of the cervical vertebrae. Altogether there are 19 muscles acting with rather short lever arms. Moreover, the neck portion contains, in a reduced space, vertebrae, ligaments, muscles, nerves and glands, all in a surprising function and interactivity. Moreover, the final tract of the spine has a natural lordotic curve, with a frontward convexity, which is important for correct absorption of movements.

All these elements of complexity are in a perfect balance which, as can be guessed, allows to achieve excellent functionality, but which is also rather critical and delicate and hence, due to traumatic events or prolonged incorrect postures, it may be impaired, causing unwelcome symptoms.

Very often the appearance of the first disorders is linked to an incorrect posture, possibly maintained for a long time (for example many hours in front of a computer terminal), which causes abnormal contractions of the neck muscles, which unduly load the spine elements and the relative intervertebral discs.

The symptoms of "cervical inflammation" then worsen and become chronic over time, because an exacerbation of the inflammation occurs, due to further muscular contraction. As a matter of fact, as a reaction to pain, the individual suffering from cervical pain tends to contract the neck muscles, which further stresses the cervical area, worsening the painful symptoms.

FIG. 1 shows a diagram of the forces acting on the cervical tract of the spine: as it can be seen, the force M imparted by the muscle fascicles of the neck to support the head—i.e. to balance weight force P, which acts on centre of gravity CG of the skull, with respect to the rotation fulcrum—discharges onto the cervical vertebrae. In particular, this muscle force expresses itself through a vector M which may ideally be decomposed into a vertical component, suitable to balance weight force P (the two forces acting through respective arms 1 and 2 with respect to the rotation fulcrum), and a horizontal component, which discharges transversely onto the cervical vertebrae producing shear stress.

The greater contraction of the muscles, due to pain, causes an increase of such force M, which remarkably worsens the condition of load on the intervertebral discs, which is the origin of the painful symptoms.

As a matter of fact, it has been observed, finding evident experimental proof thereof, that contractures and muscular spasms of these muscles of the cervical spine are one of the fundamental causes of the dysfunctions and of the painful events affecting some individuals.

Therefore, up until today, as a non-pharmacological corrective measure, it has been resorted to physiotherapeutic applications and to mechanical systems to lighten the load on intervertebral discs. One of the most widespread mechanical systems consists of rigid or inflatable orthopaedic collars.

As can be well understood, orthopaedic collars are not welcome by most people, especially if a long-term treatment is provided. As a matter of fact, they are bulky and uncomfortable to wear—both because they prevent head movements, and because they limit the body's natural breathing of the neck portion—as well as being aesthetically unpleasing and conspicuous.

SUMMARY OF THE INVENTION

The object of the present invention is hence that of providing a relaxant device which allows to prevent or reduce the problems stemming from cervical inflammation, which is easy to use, even without a specialist's consultation, which is little invasive and conceptually comfortable to wear.

BRIEF DESCRIPTION OF THE DRAWING FIGURES

Further features and advantages of the device according to the invention will in any case be more evident from the following detailed description of some preferred embodiments of the same, given by way of example and shown in the accompanying drawings, wherein:

FIG. 1, as already mentioned, is a diagrammatic view showing the balance of forces in a human skull;

DETAILED DESCRIPTION OF THE INVENTION

The present invention originates from a genial insight of its inventor who, addressing the problem, has broken the existing prejudice existing on the same. As a matter of fact, in order to solve cervical pain, it has always been believed necessary to lighten the load resting on the cervical tract of the spine. As a matter of fact, this is the object of orthopaedic collars and of other mechanical therapeutic systems designed so far.

On the contrary, through an accurate bio-mechanical study, the inventor has detected that it was not strictly necessary to lighten the resting load, but that it was instead much more advantageous to act so as to relieve the muscular tension acting on the first vertebrae.

For such purpose, the inventor has realised that it would be useful to exploit a suitable balancing of the forces acting on the skull, even applying an additional load which, skilfully applied, would succeed in relieving the actual load on the intervertebral discs rather than increasing it.

Figure 1:
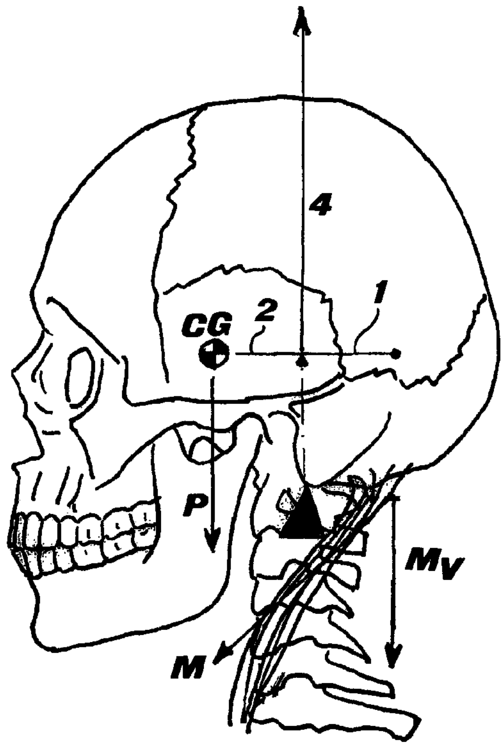
Figure 2:
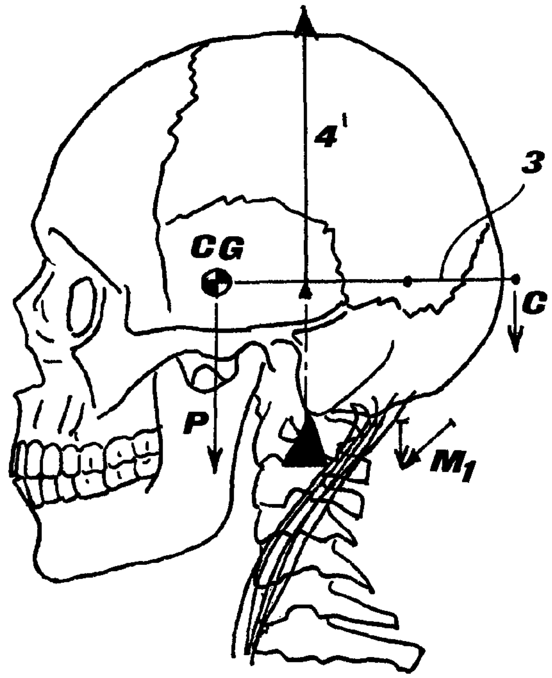
FIG. 2 is a similar view to the one of FIG. 1 wherein, according to the invention, a counterweight is applied to the rear part of the skull.

The reason of this apparent paradox can easily be explained by referring to FIGS. 1 and 2.

As can be seen in FIG. 1, weight force P of the skull, acting on its centre of gravity CG, is balanced—with respect to the rotation fulcrum lying in correspondence of the joining of the skull to the first vertebra—by the force M imparted by the muscle fascicles of the neck. Force M acts with a rather short lever arm 1 and causes a significant overall vertical load 4 (given by the sum of weight force P and of the vertical component $M_V$ of muscle force M) on the cervical tract. Moreover, as already mentioned, the vector of force M also has a horizontal component, which imparts a harmful shear action onto the vertebrae.

FIG. 2 shows instead a case wherein, according to the invention, a weight C is applied to the back part of the skull. This additional load allows to balance the weight of the skull itself, with respect to the fulcrum, and it hence allows to relieve a good deal of the tension M of the muscle fascicle. Moreover, lever arm 3 of weight C with respect to the fulcrum is remarkably longer than lever arm 1 shown in FIG. 1: hence the vertical component of weight C can be remarkably smaller than the component $M_V$ required in the natural case (FIG. 1), which produces an overall vertical load 4' (given by the sum of the weight of skull P, of the minimal, residual, vertical component of $M_1$ and of weight C) which is smaller than the natural conditions shown in FIG. 1.

Therefore, a suitably sized and arranged weight C, in actual fact determines not only an easing of the overall vertical load on cervical vertebrae, but also a strong reduction of the vector of muscle tension $M_1$ and hence of the undesired shear component thereof.

In substance, the application to the skull of a device which allows to arrange a counterweight in the rear part of the skull—the size and entity of which counterweight is a function of the position of the centre of gravity of the skull with respect to the rotation fulcrum thereof—enables to reach perfectly the objects set forth in the preliminary remarks.

In other words, the relaxant effect is achieved through a device comprising a functional support to be worn on the head and through a preferably adjustable balancing load or mass, of such an entity and position as to balance the weight of the head (and of the functional support) and to shift the centre of gravity of the same (which is of course in a rather forward position) substantially in correspondence of the articulation fulcrum on the cervical column.

The functional support may have the shape of any object which can be worn on the head, preferably an object which already has a conventional function of its own, so that it is not necessarily perceived at once as a therapeutic implement. Therefore the functional support may be in the shape of an elastic band (possibly of a spongy material for sports use), of a hat, of a protective helmet (work helmet, motorcycle helmet, . . . ) or else.

Generally, in case the support to be worn on the head has a negligible mass of its own, it is provided for the balance load to be in the shape of a significant mass (normally from 200 to 700 gr) concentrated and intended to be located in the rear part of the head.

According to a first embodiment of the invention, counterweight C, for example a series of lead plates of a weight ranging between 30 and 550 grams, is inserted in a band suitable to be worn on and fastened to an individual's head. The counterweights may also consist of gel-embedded lead pellets or other materials having a high specific weight, so as to have a suitable weight without considerable volumes.

Figure 3:
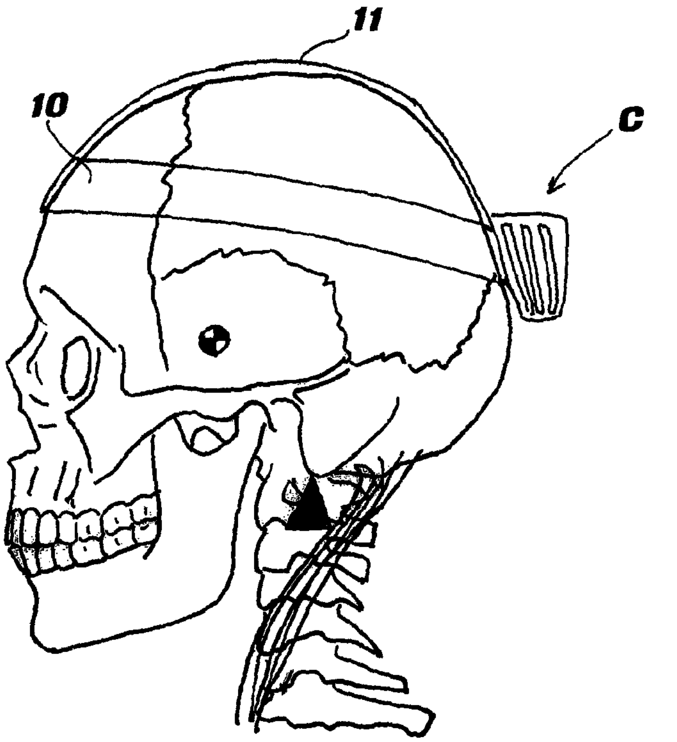
FIG. 3 is a diagrammatic view showing a first embodiment of the invention.

According to another embodiment illustrated in FIG. 3, counterweight C, in the shape of small lead plates $C_L$, is inserted in a housing of a circumferential band 10, made of fabric or leather or other suitable and pleasant material, coupled with another polar band 11, which encloses the upper part of the skull and connects the front part of circumferential band 10 through the rear part of the same.

Figure 4:
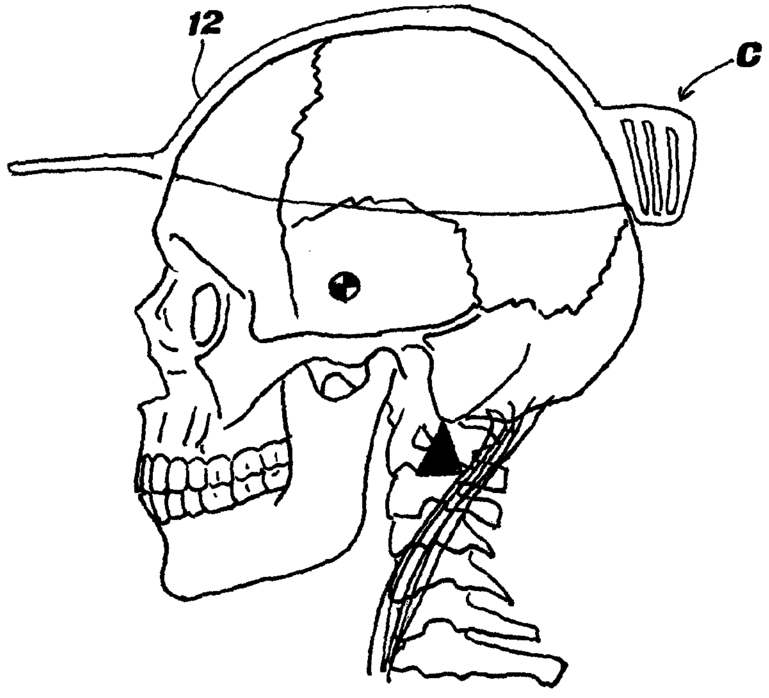
FIG. 4 is a view as in FIG. 3 showing another embodiment of the invention.

According to an alternative embodiment (FIG. 4), counterweight C is inserted in a pocket obtained in the rear portion of a hat 12.

Evidently, other may be the forms taken up by the device according to the invention, provided they are capable of supporting a counterweight having a CG in the rear part of the skull, at a suitable distance from the centre of gravity thereof.

The adjustable weight or ballast applied to the rear part of the device, or in any case arranged to balance the centre of gravity of the head, can be restrained in any way. Although it is conceivable also to hang the weight or to have more complex systems, even provided with stretchable elastic elements, to balance the head in a multitude of postural conditions, it has been detected that the user generally does not tolerate complex mobile or elastic mechanisms.

Therefore, the balancing mass is preferably concentrated (for example extending across an area not exceeding 10 $cm^2$ and preferably below 6 $cm^2$, having a volume not exceeding 10 $cm^3$) and closely and securely anchored to the device to be worn, be it a cap, a band, a helmet or any other object. Accordingly, it is preferable for the same support to be worn on the head to be fastened as securely as possible to the head, so that the inertial forces acting on the load, due to the movements, do not cause annoying displacements and shakes.

Hence the supporting functional element to be worn is advantageously provided with additional fastening means, such as adjustable and lockable laces, which may be worn both around the skull and under the chin.

Moreover, for such purpose, if the balancing mass can be decomposed into individual units—so as to guarantee load adjustability—there are provided means for mutual fastening between the units, such as adhesive layers, disengageable means of mutual engagement, and so on, to prevent the individual mass units from moving with respect to one another.

The overall balancing mass is further retained on the device to be worn by releasable retaining means (snap-on fasteners, magnetic pairs, lever blocks, . . . ) or steadily inserted in a suitable pocket of the device. For such purpose, the pocket may be provided with means which adjust the housing volume to the size of the load contained therein, so as to prevent shakes or undesired displacements within the same. For example, a rigid pocket (for example embedded within a motorcycle helmet) may have a hinged, rigid cover, which provides access to a retaining compartment. The compartment bottom is apt to translate against the thrust of rear-lying springs having a high elastic constant, between a position of maximum extension—which defines the smallest size of the compartment—and a position of maximum compression—which defines the maximum size of the compartment/pocket. Thereby, a small mass may be inserted into the pocket, which remains steadily retained in the compartment, as does a larger mass which, upon introduction into the pocket, pushes the bottom and creates the necessary space for itself in the pocket compartment.

A particularly advantageous application is in association with a protective helmet, for example a motorcycle helmet, a building site helmet or also a military helmet (for example helicopter helmets). According to another embodiment of the invention, hence, there is provided a helmet equipped with a rear compartment (for example between the rigid outer layer and the inner filling layer) wherein suitable counterweights are embedded.

According to another variant, a counterweight is instead provided, suitably shaped to make it aesthetically acceptable, to be applied to the surface of a helmet, as already said, or with temporary means (for example hook-and-loop fasteners) or with dedicated and suitably designed means (for example connection pins). Preferably, this counterweight may be conceived as a real accessory of a helmet, also providing it with a light-reflecting surface which adds an important function to the helmet, being better visible from behind also at night time.

When there is a need to equip a helmet with other tools (for example caving lights, tracking oculars, instruments for night vision, and so on), the above-mentioned accessory may be advantageously configured as a frame housing, in its front or middle part, the auxiliary equipment and, in the rear part, the counterweight according to the invention.

The effectiveness of the device according to the invention, as can be understood, is the greater, the more the counterweight can be arranged so as to suitably balance the head weight (in addition to the weight of the headgear, of the support and of the relative accessories) of the individual on whom to act, with respect to the fulcrum position. This implies the identification of the weight and position of the centre of gravity in each specific case.

From a theoretical point of view, for an accurate definition it is possible to resort to instrumental measurements, for example also by resorting to image acquisition through nuclear or echographic magnetic resonance, which certainly require the intervention of skilled medical staff.

Instead, without having to resort to complex systems, according to a preferred embodiment of the invention, the device is equipped with a plurality of different counterweights, for example three, which may be chosen based on general instructions obtained on a representative sample of the population. For example, the on average most suitable counterweight may be chosen according to age, gender and height of the individual. Evidently, in this case the most effective results may not be obtained, but nevertheless the nature itself of the device according to the invention, which is substantially free from contra-indications (provided the counterweights range within reasonable limits, for example up to 700 grams), leads to rule out any possibility of harming the individual. This, on the other hand, makes the device particularly simple and handy to use, since it does not force the individual to a medical consultation for the application thereof.

A further application which the Applicant has ascertained to be of particular advantage, is on work helmets. As a matter of fact, these are used for many consecutive hours and, on top of that, they often bear unevenly distributed loads (lamps, protections, tools, optoelectronic tracking devices, and so on). The use of these elements generally causes muscular contractures, which in the long run produce inflammations and pain.

Hence, a work helmet suitably loaded in the rear part with a balancing mass, in the way taught here, produces advantageous effects on workers.

The device according to the invention has already been tested on volunteers.

During the experimental check of the device effectiveness, it has been found that the patients receiving the test quickly experience an evident improvement. As soon as the relaxant effect is effective, the patient clearly expresses his or her wellbeing and possibly asks for adjustment of the applied load: often the request is towards increasing the load, but sometimes it is also the opposite.

The relaxant effect was clearly visible in the examined individuals also through known investigation techniques, such as echography, electromyography and muscular magnetic resonance or other experimental techniques (see for example Vasavada, Peterson, Delp "Three-dimensional spatial tuning of neck muscle activation in humans"; Exp Brain Res (2002) published on 18 Oct. 2002 by Springer-Verlag 2002).

For the determination of the load or of the balancing mass to be applied, an optimal methodological approach was also implemented, as follows.

The patient is invited to relax his neck muscles and to abandon the head, which naturally tends to incline forward (since the natural centre of gravity is shifted forward with respect to the fulcrum). The head is supported under the chin. The operation is repeated several times, until the patient learns to fully relax his muscles.

The support under the chin may be advantageously achieved through a scales device, wherefrom it is possible to obtain an indication of the head weight which the patient was able to effectively unload. The scales device has a twofold function: on the one hand it allows to understand if the patient is actually learning to relax his neck muscles, on the other it provides a first indication on the counterweight which will have to be applied to balance the head.

At this point a trial device equipped with a first load is applied to the rear of the head, of a weight equal to a preset minimum (for example 200 gr) and it is then checked if it is sufficient to obtain full balance of the head with relaxation of the patient's muscles. Otherwise, the weight is increased until a condition of substantial balance is achieved.

The load thereby determined is then applied to a final device to be worn, for example a hat to the patient's liking.

The same procedure is repeated after a few weeks, for example after a couple of months, to adjust again the load according to the new conditions whereto the patient has adapted.

As can be understood, the device according to the invention fully achieves the objects set forth in the preliminary remarks.

As a matter of fact, through a simple counterweight arranged behind the skull, it is possible to prevent and effectively alleviate the symptoms of cervical inflammation.

Thanks to the use of the device according to the invention, it is possible to alleviate the work of the 19 muscles which are involved in head control, with a very effective relaxant action. On the other hand, it has been detected that this relaxant effect acts beneficially also on the entire cervical district, as well as on the thoracic cage, itself partly affected by muscles acting on the spine.

The relaxation of the neck muscles, in addition to reducing any inflammation process, solves a whole series of side effects, such as headaches which are perceived on the temples, or dizziness related to the inflammation of the vestibular canal.

Advantageously, its ease of use and functionality make it particularly well-suited also for preventive use: as a matter of fact, the device of the invention may be worn by anybody (for example any videoterminal operator) with the scope of achieving a relaxation of the neck muscles and hence of avoiding intervertebral compressing or abnormal vertebral loads which, in the long run, would cause cervical pain.

Moreover, a support for a counterweight to be applied to the skull of an individual may be manufactured at a very accessible cost and with an aesthetically pleasing shape. By using counterweights having a high specific weight, the support can have a minimum bulk and hence a negligible impact on the individual who is to wear it, which allows to use it also for several hours in a row and in the most diverse conditions (also during working hours) with no discomfort.

It is understood, however, that the invention is not limited to the particular embodiments illustrated above, which represent only non-limiting examples of the scope of the invention, but that a number of variants are possible, all within the reach of a person skilled in the field, without departing from the scope of the invention.

For example, in particular cases, the device according to the invention may take up the features of a real semi-permanent prosthesis, to be applied possibly through surgery.

The invention claimed is:

1. A method of relaxing neck muscles to reduce inflammation of the cervical district in human being, comprising:

applying a support of a skull on a head;

balancing mass with a weight concentrated and securely fastened to said support; and arranging a centre of gravity of the mass being in a rear portion of the support, to arrange an overall centre of gravity of the head and the weight in correspondence of a rotation fulcrum of the head on a cervical spine, the weight having a weight, an area and a volume so as to balance a weight of the skull with respect to the fulcrum of the head on the cervical spine, hence relieving tension M of a muscle fascicle, the weight being smaller than a vertical component My of a muscle force in a natural case, the weight hence also determining an overall vertical load on the cervical spine which is smaller than the natural case, wherein the weight is between 30 and 550 grams, and the area does not exceed 10 $cm^2$.

2. The method as claimed in claim 1, wherein said support has a shape of a headgear.

3. The method as claimed in claim 1, wherein said support has a shape of a protection helmet.

4. The method as claimed in claim 3, wherein said weight is embedded in an accessory to be applied to the helmet surface.

5. The method as claimed in claim 4, wherein said accessory further has at least a light-reflecting surface intended to be directed to the rear of the helmet during use.

6. The method as claimed in claim 1, wherein said support has a shape of a prosthesis.

7. The method as claimed in claim 1, wherein said weight is made of a material having a high specific weight.

8. The method as claimed in claim 7, wherein said weight has a shape of gel-embedded lead pellets.

9. The method as claimed in claim 1, wherein said weight is adjustable and may be decomposed into subunits, said subunits being securely lockable one to the other by mutual fastening.

10. The method as claimed in claim 1, wherein the support has a shape of a frame provided with vision and tracking equipment.

11. The method as claimed in claim 1, wherein the method achieves relaxation of the muscles of the cervical spine of a human being.

12. The method as claimed in claim 1, wherein the volume does not exceed 10 $cm^3$.

* * * * *